United States Patent [19]

Wilke et al.

[11] 3,948,264
[45] Apr. 6, 1976

[54] INHALATION DEVICE

[75] Inventors: George A. Wilke, Evansville, Ind.; Norman C. Henderson, Columbus, Ohio; Stanley M. Stansell, Columbus, Ohio; Paul E. McCrady, Columbus, Ohio

[73] Assignee: Mead Johnson & Company, Evansville, Ind.

[22] Filed: May 21, 1975

[21] Appl. No.: 579,525

[52] U.S. Cl. ................. 128/266; 128/208; 128/209
[51] Int. Cl.² ......................................... A61M 15/00
[58] Field of Search ........... 128/266, 206, 208, 209; 222/202

[56] References Cited
UNITED STATES PATENTS

| | | | |
|---|---|---|---|
| 3,795,244 | 3/1974 | Lax et al. | 128/266 |
| 3,807,400 | 4/1974 | Cocozza | 128/266 |

FOREIGN PATENTS OR APPLICATIONS

| | | | |
|---|---|---|---|
| 505,863 | 5/1939 | United Kingdom | 128/266 |

*Primary Examiner*—Robert W. Michell
*Assistant Examiner*—Henry J. Recla
*Attorney, Agent, or Firm*—David J. Mugford; George A. Mentis; Samuel J. DuBoff

[57] ABSTRACT

A device utilized for the inhalation of medicament in a powder form. This device has a body portion with communicating primary and secondary air inlet channels and an outlet channel. The secondary inlet channel provides an enclosure for a capsule containing medicament and the outlet channel is formed in a mouthpiece protruding from the body portion. A capsule piercing structure is provided, which upon rotation puts holes in the capsule, so that upon vibration of the capsule, caused by an electro-mechanical vibration means, medicament is ejected from the capsule. After piercing and upon inhalation through the mouthpiece, and activation of the vibration means, powder is ejected into the airstream passing through the inlet channels, outlet channel, and into the user's mouth.

7 Claims, 5 Drawing Figures

U.S. Patent   April 6, 1976   3,948,264
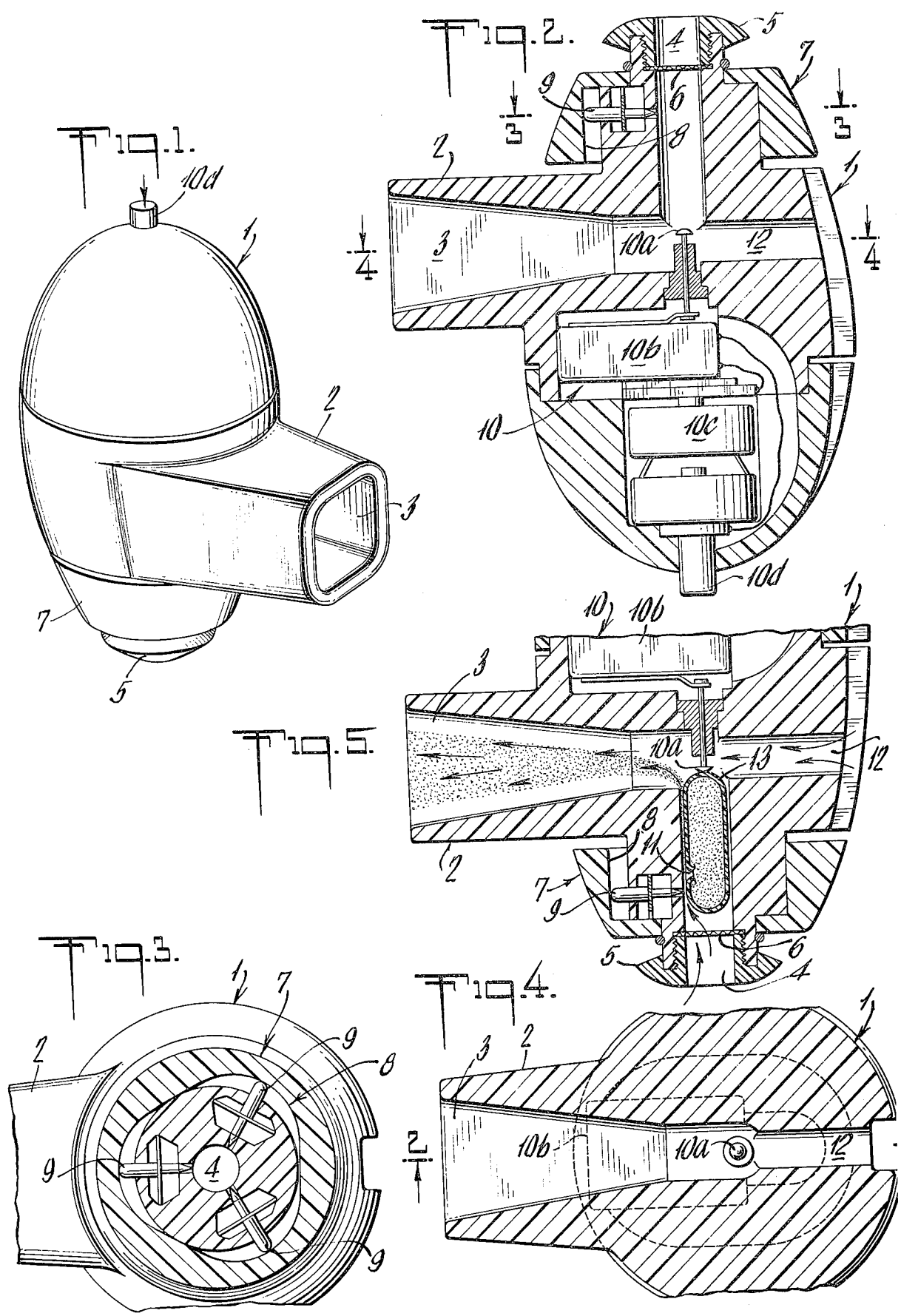

INHALATION DEVICE

This invention relates to inhalation devices. More particularly, this invention relates to inhalation devices which utilize an electrically driven vibratory mechanism for causing medicament to be ejected from a capsule into a stream of inhaled air.

Certain diseases of the respiratory tract are known to respond to treatment by the direct application of therapeutic agents. As these agents are most readily available in dry powdered form, their application is most conveniently accomplished by inhaling the powdered material through the nose or mouth. This powdered form results in the better utilization of the medicament in that the drug is deposited exactly at the site desired and where its action may be required; hence, very minute doses of the drug are often equally as efficacious as larger doses administered by other means, with a consequent marked reduction in the incidence of undesired side effects. Alternatively, the drug in this form may be used for treatment of diseases other than those of the respiratory system. When the drug is deposited on the very large surface areas of the respiratory tract, it may be very rapidly absorbed into the blood stream; hence, this method of application may take the place of administration by injection, tablet, or other conventional means.

Several inhalation devices useful for dispensing this powder form of medicament are known in the prior art. For example, in U.S. Pat. Nos. 3,507,277; 3,518,992; 3,635,219; 3,795,244; and 3,807,400, inhalation devices are disclosed having means for piercing of a capsule containing a powdered medicament, which upon inhalation is drawn out of the pierced capsule and into the user's mouth. Several of these patents disclose propeller means, which upon inhalation aid in dispensing the powder out of the capsule, so that it is not necessary to rely solely on the inhaled air to suction powder from the capsule. For example, in U.S. Pat. No. 2,517,482, issued to Hall, a device is disclosed having a powder containing capsule placed in a lower chamber before inhalation, where it is pierced by manual depression of a piercing pin by the user. After piercing, inhalation is begun and the capsule is drawn into an upper chamber of the device where it moves about in all directions to cause a dispensing of powder through the pierced holes and into the inhaled air stream. U.S. Pat. No. 3,831,606 discloses an inhalation device having multiple piercing pins, propeller means, and a self-contained power source for operating the propeller means via external manual manipulation, so that upon inhalation the propeller means aids in dispensing the powder into the stream of inhaled air.

These prior art devices present several problems and posesses several disadvantages which are remedied by the inhalation devices of the present invention. For instance, these prior art devices require that the user exert extreme effort in inhalation to effect dispensing or withdrawal of powder from a pierced capsule into the inhaled air stream. With these prior art devices, suction of powder through the pierced holes in the capsule caused by inhalation does not withdraw all or even most of the powder out of the capsule, thus causing a waste of the medicament. Another most important problem which has not been solved by the prior art devices is the presence of uncontrolled amounts or clumps of powdered material being inhaled into the user's mouth, rather than a constant inhalation of controlled amounts of finely dispersed powder.

The inhalation devices of the present invention provide a control over and a consistency of powder flow because the withdrawal and dispension of powder into the inhaled air stream is not wholly dependent upon the users techniques of inhalation, but more dependent upon the mechanical characteristics of the device in causing the powder to be dispensed. Other advantages of the devices of the present invention are the ease of use of these devices because of their one-piece construction, the elimination of involuntary dispensing of powder, the capability of variation of dispension characteristics of the device in accordance with the type of powder being dispensed, the elimination of the necessity to rely on the user's inhalation totally for dispension of powder, and the more complete dispension of powder from the capsules.

It has now been found that the above-mentioned advantages of an inhalation device are provided by an inhalation device, for the dispensing of medicament in a powder form, having a body portion comprising an air outlet channel in one end of the body portion providing a mouthpiece for inhalation of air by the user; a primary air inlet channel in another end of said body portion communicating with said air outlet channel; a secondary air inlet channel in a third end of the body portion providing an enclosure for a capsule containing the medicament, said secondary inlet channel communicating with said primary air inlet channel and said outlet channel; means for piercing holes in the capsule disposed around the secondary inlet channel; and electromechanical means for vibrating the capsule, whereby after piercing of the capsule, upon activation of the vibrating means and inhalation, the medicament is ejected from the pierced capsule, dispersed into the stream of air inhaled through the inlet channels, and inhaled into the outlet channel and the mouth of the user.

A preferred embodiment of the inhalation devices of the present invention is shown in the following drawings, wherein:

FIG. 1 is a perspective view of an inhalation device embodied in this invention;

FIG. 2 is a longitudinal, cross-sectional view of the device shown in FIG. 1, taken through lines 2—2 of FIG. 4;

FIG. 3 is a cut-away, cross-sectional view of the device shown in FIG. 1, taken through line 3—3 of FIG. 2;

FIG. 4 is a cut-away, cross-sectional view of the device shown in FIG. 1 taken through line 4—4 of FIG. 2;

FIG. 5 is a cut-away, cross-sectional view of the device of FIG. 1, similar to FIG. 2, showing the mode of operation of the inhalation device of the present invention.

Referring now to the drawings of the present case, particularly FIG. 1, this embodiment of the device of the present invention comprises an egg-shaped body portion 1. About one third of the distance from the top of this device, when in the "use" position, protrudes outwardly a mouthpiece 2 for use during inhalation. Within this mouthpiece 2 is an air outlet channel 3.

As shown in FIG. 2, air outlet channel 3 is generally aligned with and meets a primary air inlet channel 12 which together meet a secondary air inlet channel 4 generally at a generally right angle to channels 3 and 12. In the "use" position, the secondary inlet channel is disposed within the bottom end of this device.

When the device is inverted, as shown in FIG. 2, a powder-filled capsule 13 (shown in FIG. 5) is dropped into inlet channel 4 and a slip-on cap 5 is placed over the outermost end of inlet channel 4. Cap 5 at its innermost end has a screen 6 extending across inlet channel 4 which prevents the capsule from falling out yet allows air to be admitted through channel 4. With cap 5 secured onto body portion 1, the capsule inserted in channel 4 is slightly shorter in length than channel 4, so that about one eighth of an inch space exists between the end of the capsule and the juncture of air inlet 4 and outlet 3.

Disposed around inlet channel 4 below screen 6 is a piercing means, generally designated 7. Piercing means 7 consist of a trochoidal chamber 8 as shown in FIG. 3, having three radially mounted, spring-biased piercing needles 9 mounted therein. Upon hand rotation of chamber 8, simultaneous inward radial motion of needles 9 occurs because of this trochoidal shape of the inner surface of chamber 8, against which the bases of needles 9 are held by spring pressure. Further rotation of chamber 8 allows the needles 9 to be retracted by their spring mountings to their original position, so that upon piercing and subsequent withdrawal of needles 9 from the capsule, holes 11 (one hole is shown in FIG. 5) remain in the capsule from which powder will be ejected, upon inhalation and activation of an electro-mechanical vibrating means, generally designated 10.

Electro-mechanical vibrating means 10 has at its innermost end a vibrating plunger rod 10a, which projects into the intersection of inlet channel 4 and outlet channel 3. As previously stated, while the device is not in use, the end of rod 10a is about one eighth of an inch away from the end of the capsule placed in inlet channel 4. Connected to plunger rod 10a is a solenoid buzzer 10b, which causes vibration of rod 10a. Buzzer 10b is powered by a high energy electric cell 10c, which is activated by an external switch 10d.

Upon placing a capsule 13 in inlet channel 4 and securing cap 5 onto body portion 1, piercing means 7 is rotated to cause piercing of the capsule so that powder may now be dispensed. The device is then inverted so that the capsule lies against screen 6 as shown in FIG. 5. Upon inhalation through outlet channel 3 and concurrent pressing of switch 10d to activate the electro-mechanical vibrating means 10, air is sucked through inlet channels 4 and 12, the air stream through the secondary inlet channel 4 raises the capsule up against vibrating plunger rod 10a. The capsule is thus vibrated rapidly with powder being fluidized and dispensed from the pierced holes therein. The air stream through inlet channel 4 and 12 aids in withdrawal of powder from the capsule and carries this powder through outlet channel 3 to the mouth of the user.

The medicament containing capsules which may be utilized in the devices of the present invention can be of a standard gelatin material or formed from any material which is inert to the product contained therein and able to be satisfactorily punctured. The medicament contained in this capsule may be useful for treatment of several respiratory illnesses. For example, medicaments useful as bacterial vaccines, sinusitis vaccines, antihistaminic agents, vaso-constricting agents, anti-bacterial, or anti-asthmatic agents, which are used in finely particulate form and packaged in a capsule, may be dispensed from the inhalation devices of the present invention. It is preferred in particular to dispense powders of theophylline, aminophylline, and di-sodium cromolyn from the inhalation devices of the present invention.

As disclosed in U.S. Pat. Nos. 3,155,573; 3,624,582; and 3,419,578, the effectiveness of a medicament for the treatment of an illness depends greatly upon the effectiveness of dispension of the powder during inhalation, which in turn, depends greatly upon the particle size of the powder and the area of the respiratory system where it is desired that the powder be deposited. It is intended that the inhalation devices of the present invention can be varied in structure, from the device described above, by utilizing ordinary skill in the art to meet the demands of particular medicaments for particular purposes.

For example, the shape and location of structures in the inhalation device described above can be varied so that the capsule may be enclosed within the outlet channel, rather than the air inlet channel, and the electro-mechanical means may then be at a right angle to the inlet channel. It may be desired, in order to alter the powder dispensing characteristics of the device, not to have the vibrating plunger rod strike the capsule at its end, but at some other point. Further, the components of the electro-mechanical vibrating means do not have to be placed in the particular sequence shown but can be separated, if necessary.

Although the piercing means disclosed utilizes a trochoidal chamber having spring-biased piercing needles, the shape of this rotatable chamber and number of needles can be altered, as long as the needles can be moved radially inwardly to the capsule and then retracted to leave pierced holes in a capsule enclosed in one of the channels.

The electro-mechanical vibrating means disclosed above is preferred, however, any conventional mechanism which could be connected to a plunger rod to cause vibration of the rod and consequent vibration of the capsule contained in this device could be utilized, such as for example, a motor with a cam arrangement.

The advantages of the inhalation devices of the present invention occur generally because the dispension of powder desired is not effected predominantly by the user's technique of inhlation, but rather by the pounding action of the vibrating means upon the capsule to first cause ejection of powder out of the capsule. Thus, by variation of the amplitude and frequency of vibrations of this electro-mechanical means, the dispensing characteristics of the device can be regulated.

Further control over dispension can be achieved with the devices of the present invention because of the inter-relation between inhalation and activation of the electro-mechanical vibrating means as desired. Because of this generally one eighth inch space between the capsule and vibrating means, vibration of the capsule and ejection of powder therefrom can be regulated according to the user's desires during inhalation and involuntary vibration of the capsule can be eliminated.

In order to illustrate the advantages of the inhalation devices of the present invention, the inhalation device described above was tested against an inhalation device disclosed in the prior art; namely, U.S. Pat. Nos. 3,507,277 and 3,518,992. The particular device tested is available from Fisons Pharmaceutical Limited, Loughborough, England, under the name "Spinhaler."

The test was conducted to determine the amount of powder dispensed by each device per number of mechanical inhalations. A capsule, containing a 40:60 blend of acetylcysteine and lactose was used in each device for a minimum of two tests. Identical inhalations of one cubic foot per second for two seconds were incurred, and after each inhalation the capsule was removed and weighed, so that the amount of powder dispensed could be determined.

The following test will compare the "spinhaler" device with the device disclosed in FIGS. 1–5 of the present invention, identified below as "Tested." Each device will be measured for number of milligrams (mg) of powder inhaled per number of inhalations. Three of the above-identified capsules were tested in each device, however, the capsule in each device showing the most erratic result has been omitted.

| Number of Inhalations | Capsule | Number of Mg Powder Inhaled | |
|---|---|---|---|
| | | "Spinhaler" | "Tested" |
| 1 | 1 | 1.8 | 3.4 |
| | 2 | 5.4 | 6.5 |
| 2 | 1 | 2.8 | 4.4 |
| | 2 | 7.7 | 7.0 |
| 3 | 1 | 2.9 | 4.3 |
| | 2 | 5.0 | 6.9 |
| 4 | 1 | 4.4 | 4.4 |
| | 2 | 5.8 | 10.6 |
| 5 | 1 | 4.2 | 3.8 |
| | 2 | 5.6 | 7.4 |
| 6 | 1 | 7.0 | 4.6 |
| | 2 | .6 | 6.0 |
| 7 | 1 | 9.0 | 6.0 |
| | 2 | 2.6 | 9.0 |
| 8 | 1 | 4.6 | 3.4 |
| | 2 | .6 | 12.0 |
| 9 | 1 | 2.4 | 3.0 |
| | 2 | 4.4 | 3.4 |
| 10 | 1 | 1.8 | 3.2 |
| | 2 | 3.7 | 1.6 |

The test on the "Spinhaler" device using Capsule 1 shows a pattern of gradual build-up and the decline in powder dispensed. The tests on this device using Capsule 2 shows a generally erratic pattern. By comparison, the tests on the "Tested" device using Capsule 1 shows a generally uniform pattern of dispension and on Capsule 2, a generally increasing pattern of powder dispension.

These results indicate that the "Spinhaler" appears to be more erratic in operation than the "Tested" device and to be less effective in total amount of powder dispensed.

What is claimed is:

1. An inhalation device, for the dispensing of medicament in a powder form, having a body portion comprising an air outlet channel in said body portion providing a mouthpiece for inhalation of air by the user;
a primary air inlet channel in said body portion communicating with said air outlet channel;
a secondary air inlet channel in said body portion providing an enclosure for movement therein resulting from said air inhalation of a capsule containing said medicament, said secondary inlet channel communicating with said primary air inlet channel and said outlet channel;
means for piercing holes in said capsule disposed around said secondary inlet channel; and
electro-mechanical means for vibrating said capsule, whereby after piercing of said capsule, upon activation of said vibrating means and inhalation, said medicament is ejected from said pierced capsule, dispersed into the stream of air inhaled through said inlet channels, and inhaled into said outlet channel and the mouth of the user.

2. An inhalation device according to claim 1 wherein said primary air inlet channel is generally aligned with and meets said outlet channel which together meet said secondary air inlet channel at a generally right angle thereto.

3. An inhalation device according to claim 2 wherein said vibrating means is disposed within said body portion at a right angle to said outlet channel and adjacent the innermost end of said secondary inlet channel.

4. An inhalation device according to claim 3 wherein said vibrating means comprises an external switch, electric power cell, solenoid buzzer, and plunger rod, whereby upon activation of said vibration means by pressing of said switch, said plunger rod vibrates against said capsule to cause powder to be ejected therefrom.

5. An inhalation device according to claim 4 wherein said piercing means comprises a rotatable chamber having radially extending, spring-biased needles mounted thereon, whereby rotation of said chamber causes said needles to pierce said capsule and then be retracted.

6. An inhalation device according to claim 5 wherein said rotatable chamber is trochoidal in shape and has three of said needles.

7. An inhalation device according to claim 6 wherein a slip-on cover cap is secured around the outermost end of said secondary inlet channel and said cap has a screened opening to permit air to be inhaled therethrough, yet prevent said capsule from falling out of the device during use.

* * * * *